(12) United States Patent
Lloyd et al.

(10) Patent No.: US 11,626,200 B2
(45) Date of Patent: Apr. 11, 2023

(54) HISTOLOGY RECOGNITION TO AUTOMATICALLY SCORE AND QUANTIFY CANCER GRADES AND INDIVIDUAL USER DIGITAL WHOLE HISTOLOGICAL IMAGING DEVICE

(71) Applicant: H. LEE MOFFITT CANCER CENTER AND RESEARCH INSTITUTE, INC., Tampa, FL (US)

(72) Inventors: Mark Cassidy Cridlin Lloyd, Tampa, FL (US); Marilyn M. Bui, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 167 days.

(21) Appl. No.: 16/792,452

(22) Filed: Feb. 17, 2020

(65) Prior Publication Data
US 2020/0184193 A1    Jun. 11, 2020

Related U.S. Application Data

(62) Division of application No. 15/698,849, filed on Sep. 8, 2017, now Pat. No. 10,565,430, which is a division
(Continued)

(51) Int. Cl.
*G06T 7/80* (2017.01)
*G16H 30/20* (2018.01)
(Continued)

(52) U.S. Cl.
CPC ......... *G16H 30/20* (2018.01); *G01N 33/5091* (2013.01); *G06T 7/80* (2017.01);
(Continued)

(58) Field of Classification Search
CPC ........ G16H 10/40; G16H 15/00; G16H 50/30; G16H 50/70; G16H 30/40; G16H 30/20; G01N 33/5091
See application file for complete search history.

(56) References Cited

U.S. PATENT DOCUMENTS

| | | | |
|---|---|---|---|
| 5,526,258 | A | 6/1996 | Bacus |
| 6,631,203 | B2 | 10/2003 | Ellis et al. |

(Continued)

FOREIGN PATENT DOCUMENTS

| | | |
|---|---|---|
| EP | 2405265 | 1/2012 |
| WO | 2010/088672 | 8/2010 |

OTHER PUBLICATIONS

International Search Report and Written Opinion, dated May 14, 2013, received in connection with International Patent Application No. PCT/US2013/022017.
(Continued)

*Primary Examiner* — Shefali D Goradia
(74) *Attorney, Agent, or Firm* — Meunier Carlin & Curfman LLC

(57) ABSTRACT

Digital pathology is the concept of capturing digital images from glass microscope slides in order to record, visualize, analyze, manage, report, share and diagnose pathology specimens. The present disclosure is directed to a desktop slide scanner, which enables pathologists to scan slides at a touch of a button. Included is a workflow for reliable imaging, diagnosis, quantification, management, and sharing of a digital pathology library. Also disclosed herein is an analysis framework that provides for pattern recognition of biological samples represented as digital images to automatically quantitatively score normal cell parameters against disease state parameters. The framework provides a pathologist with an opportunity to see what the algorithm is
(Continued)

scoring, and simply agree, or edit the result. This framework offers a new tool to enhance the precision of the current standard of care.

6 Claims, 10 Drawing Sheets

Related U.S. Application Data of application No. 14/373,277, filed as application No. PCT/US2013/022017 on Jan. 18, 2013, now Pat. No. 9,760,760.

(60) Provisional application No. 61/733,502, filed on Dec. 5, 2012, provisional application No. 61/588,215, filed on Jan. 19, 2012, provisional application No. 61/588,250, filed on Jan. 19, 2012.

(51) Int. Cl.
| | |
|---|---|
| *G16H 50/30* | (2018.01) |
| *G16H 50/70* | (2018.01) |
| *G16H 10/40* | (2018.01) |
| *G16H 15/00* | (2018.01) |
| *G16H 30/40* | (2018.01) |
| *G06V 20/69* | (2022.01) |
| *G01N 33/50* | (2006.01) |

(52) U.S. Cl.
CPC .......... *G06V 20/693* (2022.01); *G06V 20/698* (2022.01); *G16H 10/40* (2018.01); *G16H 15/00* (2018.01); *G16H 30/40* (2018.01); *G16H 50/30* (2018.01); *G16H 50/70* (2018.01); *G06T 2207/10056* (2013.01); *G06T 2207/30068* (2013.01)

(56) References Cited

U.S. PATENT DOCUMENTS

| | | | |
|---|---|---|---|
| 7,979,212 | B2 | 7/2011 | Gholap et al. |
| 9,230,063 | B2 | 1/2016 | Bhargava et al. |
| 9,729,749 | B2 * | 8/2017 | Crandall ................ G02B 21/26 |
| 2004/0114800 | A1 | 6/2004 | Ponomarev et al. |
| 2006/0067680 | A1 * | 3/2006 | Yang .................. H04N 1/00204 |
| | | | 396/535 |
| 2007/0190566 | A1 | 8/2007 | Montagu |
| 2007/0264481 | A1 | 11/2007 | DeSimone et al. |
| 2008/0304733 | A1 | 12/2008 | MacAulay et al. |
| 2010/0261811 | A1 | 10/2010 | Thomas |
| 2011/0060766 | A1 | 3/2011 | Ehlke et al. |
| 2011/0221882 | A1 * | 9/2011 | Crandall .............. G02B 21/008 |
| | | | 348/79 |
| 2012/0041274 | A1 | 2/2012 | Stone et al. |
| 2012/0262564 | A1 | 10/2012 | Marcelpoil et al. |
| 2013/0330325 | A1 | 12/2013 | Grabe et al. |
| 2020/0131565 | A1 * | 4/2020 | Tafas ................. G01N 21/6428 |

OTHER PUBLICATIONS

International Preliminary Report on Patentability and Written Opinion, dated, dated Jul. 22, 2014, received in connection with International Patent Application No. PCT/US2013/022017.

* cited by examiner

HISTOLOGY RECOGNITION TO AUTOMATICALLY SCORE AND QUANTIFY CANCER GRADES AND INDIVIDUAL USER DIGITAL WHOLE HISTOLOGICAL IMAGING DEVICE

CROSS-REFERENCE TO RELATED APPLICATIONS

This application is a divisional of U.S. patent application Ser. No. 15/698,849, filed on Sep. 8, 2017, and entitled "Histology Recognition to Automatically Score and Quantify Cancer Grades and Individual User Digital Whole Histological Imaging Device," which is a divisional of U.S. patent application Ser. No. 14/373,277, filed on Jul. 18, 2014, and entitled "Histology Recognition to Automatically Score and Quantify Cancer Grades and Individual User Digital Whole Histological Imaging Device," which is a 371 of PCT/US2013/022017, filed on Jan. 18, 2013, and entitled "Histology Recognition to Automatically Score and Quantify Cancer Grades and Individual User Digital Whole Histological Imaging Device," which claims the benefit of U.S. provisional patent application No. 61/588,215, filed on Jan. 19, 2012, U.S. provisional patent application No. 61/588,250, filed on Jan. 19, 2012, and U.S. provisional patent application No. 61/733,502, filed on Dec. 5, 2012, the disclosures of which are expressly incorporated herein by reference in their entireties.

STATEMENT REGARDING FEDERALLY FUNDED RESEARCH

This invention was made with government support under Grant No. U54CA143970 awarded by the National Institute of Health. The government has certain rights in the invention.

BACKGROUND

Pathology is the specialized scientific study of the nature of disease and the medical practice of diagnosis of those diseases. Disease is often manifested in anatomical changes which can be visually determined. Pathologists, whether surgical, cytopathological, forensic, veterinary or other, view these changes from a normal state and make a diagnosis of the disease state. For example, cancer is diagnosed by visually identifying the structural alteration of cells. In order to simplify and describe the disease, many common cancer types are graded based on the severity or aggressive phenotype of the disease. The amount of phenotypic change from normal is described in multiple grading systems including Gleason (prostate), Nottingham (breast), Fuhrman (kidney), etc.

Each of these specialized grades includes a small number of visually identifiable criteria on the hematoxylin and eosin stained microscope slide. Several tumor types are simply graded I-IV, and are based cellular differentiation (i.e., how different the cells look compared to normal). Other factors that may be considered, depending on the tumor type, are structural formation and cellular proliferation (growth rate). The histological grade often has a profound influence on clinical decision making. This practice has been traced back to von Hansemann in the 1890s. Many of the grading systems, such as the Nottingham Score for breast cancer, are as simple as three visual clues and have remained wholly unchanged since the 1920s.

Unfortunately, discrepancies have arisen between groups of pathologists on a series of equivocal cases. This is due in large part to the challenging estimation and judgment calls which need to be made under stress. For example, pathologists may use a number of properties in deciding the nature of a cell. These properties often do not have a rigid definition. Thus, a pathologist provides a pathological decision based on the pathologist's particular experience.

However, with the advent of digital histological slide scanning (1999), massively powerful computational power and robust and reliable algorithms, novel methods are being sought to grade disease states and more precisely grade many common cancer types.

Digital pathology takes advantage of high computing efficiency and large volumes of available computational storage to create digital images of glass microscopy slides enabling a virtual microscopy to outfit the pathologist's toolbox. Automated slide scanners provide pathology departments with the high throughput tools necessary to capture tens of thousands of whole slide images every year. Slide scanners automate repeatable imaging conditions for whole slides, which enables a clinic to digitally image slides and make these digital images available to all pathologists within each network system.

While high-throughput slide scanners area generally available for pathology laboratories, desktop single slide scanners are not common. Desktop scanners would enable the individual pathologist to scan slides at a touch of a button and could be integrated with specialized software tools to establish a one-stop workflow for reliable imaging, diagnosis, quantification, management, and sharing of their own digital pathology library.

SUMMARY

The present disclosure describes systems and methods that use the American Joint Commission on Cancer (AJCC) and the College of American Pathology (CAP) guidelines for qualitatively grading cancer types and translates the rules of visual identification to computational algorithms capable of accurately and consistently grading cancer. The systems and methods may aid physicians in their decision making. By offering a companion diagnostic algorithm to pathologists, the physician now has an additional tool in their arsenal to confirm, document and report potentially diagnostic data.

In accordance with the above, there is provided a computer-implemented analysis framework that provides for pattern recognition of biological samples represented as digital images to automatically quantitatively score normal cell parameters against disease state parameters in the same way the governing bodies of the AJCC and CAP recommend pathologists perform the same duties. The framework provides a pathologist with an opportunity to see what the algorithm is scoring, and simply agree, or edit the result. This framework offers a new tool to enhance the precision of the current standard of care.

In accordance with some implementations, there is provided a desktop scanning device that may be used to in conjunction with a personal computer. The desktop scanning device may be roughly the size of a standard 3-ring binder. The desktop scanning device may be used by pathologists to digitally scan, share, analyze, report or otherwise document the slides they are currently viewing.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Digital pathology is the concept of capturing digital images from glass microscope slides in order to record, visualize, analyze, manage, report, share and diagnose pathology specimens. This practice is being integrated in pathology departments to increase productivity, workflow efficiency and the ability to quantify results. In particular, slide scanners automate repeatable imaging conditions for whole slides. As will be described herein below, the present disclosure provides implementations of a desktop single slide scanner that, e.g., will enable pathologists to scan slides at a touch of a button. Furthermore, when integrated with specialized software tools, pathologists may establish a one-stop workflow for reliable imaging, diagnosis, quantification, management, and sharing of their own digital pathology library.

Figure 1:
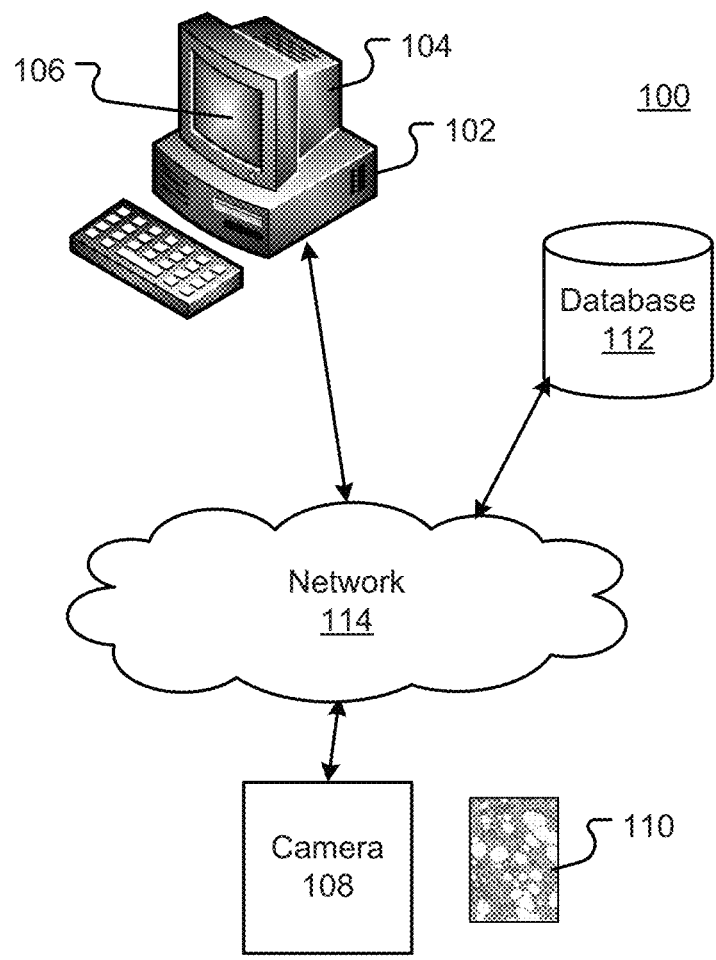
FIG. 1 illustrates an exemplary environment.

FIG. 1 is a block diagram illustrating an exemplary automated digital image based biological sample feature detection and classification system 100. The system 100 may include one or more computers 102 with a computer display 104 (only one of which is illustrated). The computer display 104 may present a graphical user interface ("GUI") 106 to a user. The computer display 104 may provide for touch-based manipulation of information, images and other user interfaces. The system 100 may optionally include a microscope or other magnifying device (not illustrated). The system 100 further includes a digital or analog camera 108 used to provide plural images 110 in various image or data formats, as will be described in other implementations with reference to FIG. 6, a slide scanner 500 may be used in conjunction with the camera 108.

One or more databases 112 may store biological sample information as digital images or in other digital data formats. The one or more databases 112 may also include raw and/or processed digital images and may further include knowledge databases created from automated analysis of the digital images 110. For example, the databases 112 may include voice annotation of records. The one or more databases 112 may be integral to a memory system on the computer 102 or in secondary storage such as a hard disk, solid state media, optical disk, or other non-volatile mass storage devices. The computer 102 and the databases 112 may also be connected to an accessible via one or more communications networks 114 and/or distributed across components connected to the communications networks 114. All memory systems and computer-readable media disclosed herein are intended to be tangible memory systems.

Figure 8:
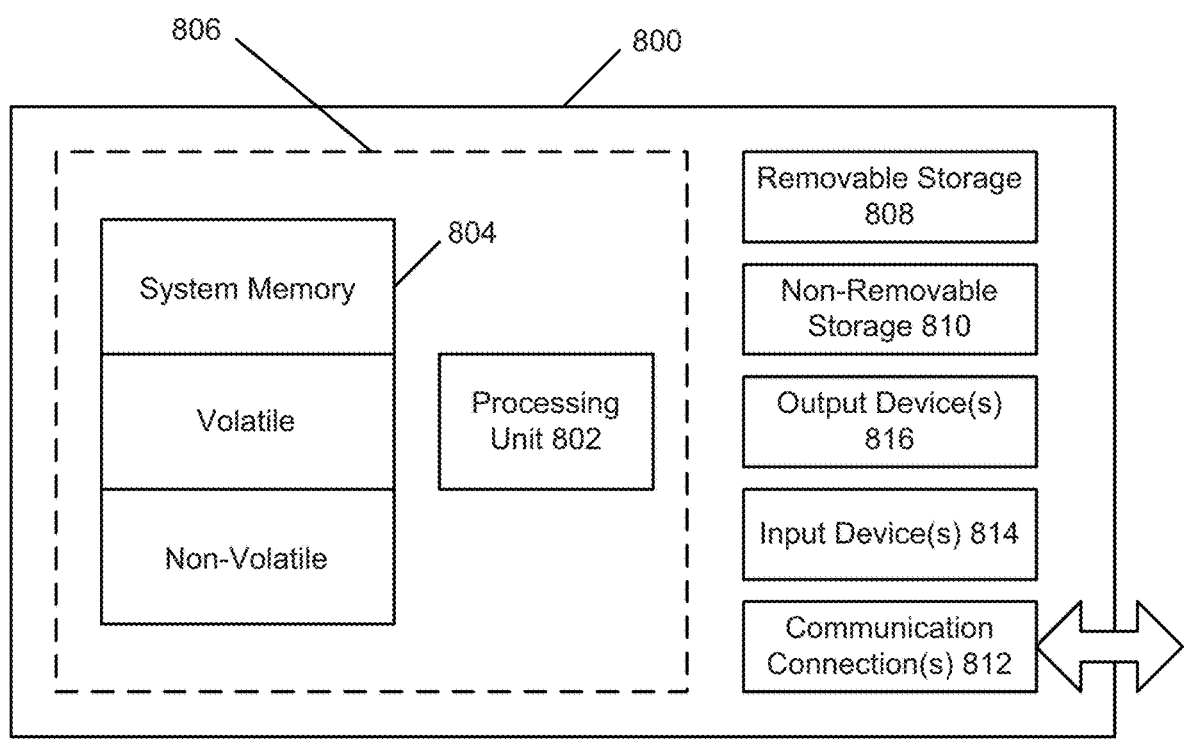
FIG. 8 shows an example computing environment.

In the above system 100, the one or more computers 102 include, but are not limited to desktop computers, laptop/notebook computers, workstations, thin clients, mobile devices, tablet computers, smart phones, personal digital assistants (PDA), Internet appliances, etc. An example computing device is shown in FIG. 8.

The communications network 114 may include, but is not limited to, the Internet, an intranet, a wired or wireless Local Area Network (LAN or WiLAN), a Wide Area Network (WAN), a Metropolitan Area Network (MAN), Public Switched Telephone Network (PSTN) and other types of communications networks 114. The communications network 114 may include one or more gateways, routers, or bridges. The communications network 114 may include one or more servers and one or more web-sites accessible by users to send and receive information useable by the one or more computers 102. The communications network 114 includes, but is not limited to, data networks using the Transmission Control Protocol (TCP), User Datagram Protocol (UDP), Internet Protocol (IP) and other data protocols.

The one or more databases 112 may include plural digital images 110 of biological samples taken with a camera such as a digital camera and stored in a variety of digital image formats including, but not limited to, TIFF (without compression). However, the present disclosure is not limited to these digital image formats and other digital image or digital data formats can also be used to practice the subject matter of the disclosure. The digital images 110 are typically obtained by magnifying the biological samples with a microscope or other magnifying device and capturing a digital image of the magnified biological sample.

Each digital image 110 typically includes an array, usually a rectangular matrix, of pixels. Each "pixel" is one picture element and is a digital quantity that is a value that represents some property of the image at a location in the array corresponding to a particular location in the image. Typically, in continuous tone black and white images the pixel values represent a gray scale value. Pixel values for a digital image 110 typically conform to a specified range. For example, each array element may be one byte (i.e., eight bits). With one-byte pixels, pixel values range from zero to 255. In a gray scale image a 255 may represent absolute white and zero total black (or visa-versa). Color digital images consist of three color planes, generally corresponding to red, green, and blue (RGB). For a particular pixel, there is one value for each of these color planes, (i.e., a value representing the red component, a value representing the green component, and a value representing the blue component). By varying the intensity of these three components, all colors in the color spectrum typically may be created.

Data may be maintained on a tangible computer readable medium including magnetic disks, solid state media, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

Term Definitions

As used herein, the term "sample" includes cellular material derived from a biological organism. Such samples include but are not limited to hair, skin samples, tissue samples, cultured cells, cultured cell media, and biological fluids. The term "tissue" refers to a mass of connected cells (e.g., central nervous system (CNS) tissue, neural tissue, or eye tissue) derived from a human or other animal and includes the connecting material and the liquid material in association with the cells. The term "sample" also includes media containing isolated cells. One skilled in the art may determine the quantity of sample required to obtain a reaction by standard laboratory techniques. The optimal quantity of sample may be determined by serial dilution. The term "biological component" includes, but is not limited to nucleus, cytoplasm, membrane, epithelium, and nucleolus and stromal. The term "medical diagnosis" includes analysis and interpretation of the state of tissue material.

As will be described in detail below, digital images 110 representing biological samples including cells, tissue samples, etc may be analyzed to provide a determination of certain known medical conditions for humans and animals. For example, digital images 110 may be used to determine cell proliferate disorders such as cancers, etc. in humans and animals. Digital images 110 may be captured by, e.g., cameras 108 provided in optical microscopes, where the digital images 110 represent the images seen by a human eye through the microscope. The images may then be stored in the one or more databases 112.

Figure 2:
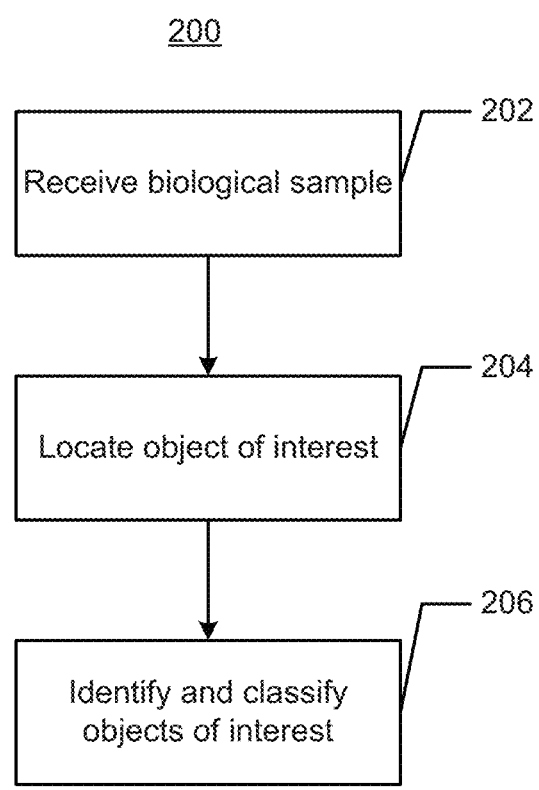
FIG. 2 is a high level operation flow diagram illustrating a method for automated biological sample analysis.

FIG. 2 is a high level operation flow diagram illustrating a method 200 for automated biological sample analysis. At 202, a digital image of a biological sample is received. The digital image 110 may be retrieved from the one or more databases 112 within the system 100. At 204, at least one object of interest is located in the digital image. As will be described below, an automated process to determine features of the biological sample represented by the digital image 110. At 206, the located biological objects of interest are identified and classified to determine a medical diagnosis or medical conclusion.

Figure 3A:
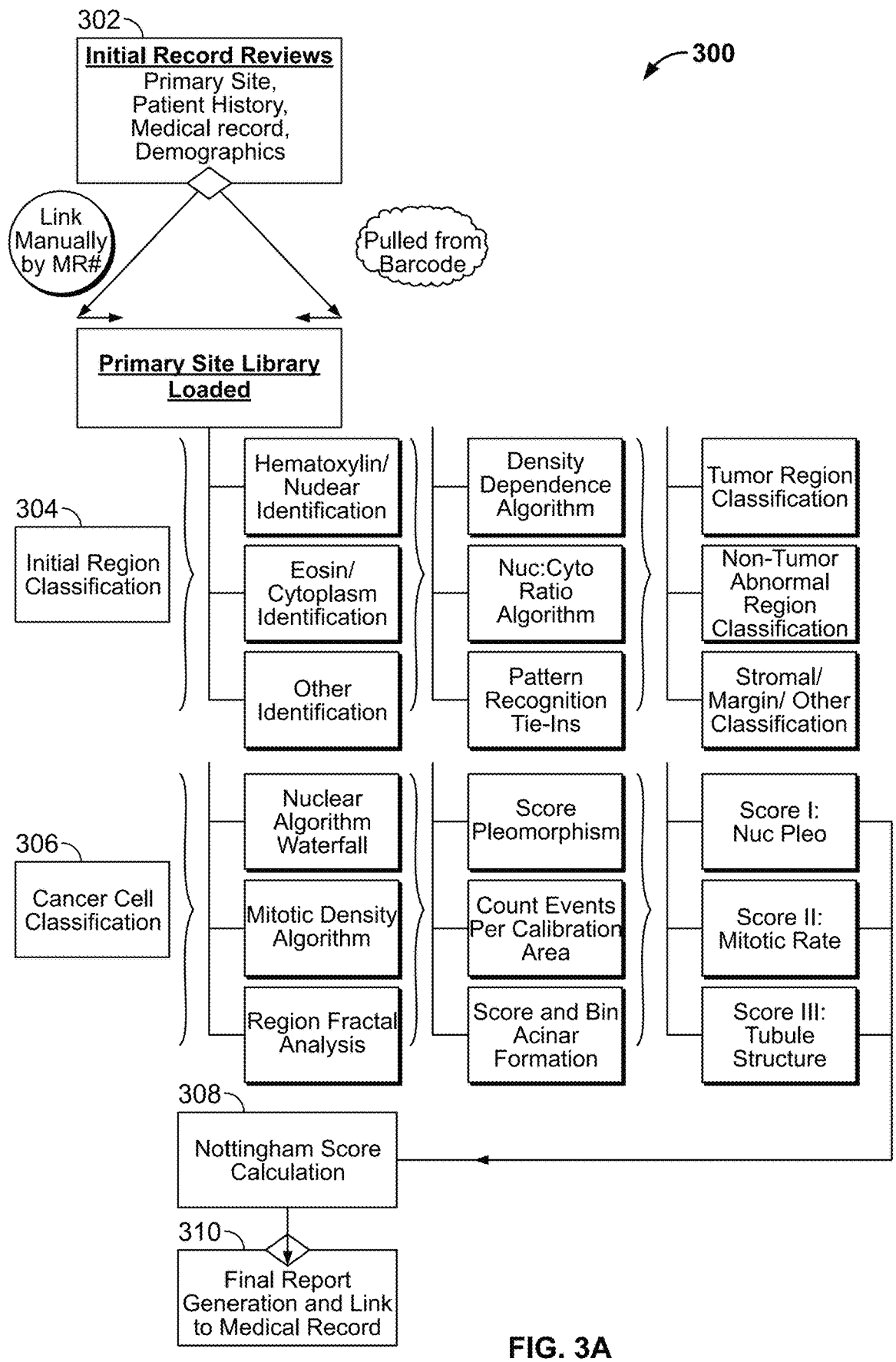
FIG. 3A illustrates an operational flow diagram that illustrates a method for the determination of features of the biological sample represented by digital images and grading such features.

FIG. 3 illustrates an operational flow diagram that illustrates a method 300 for the determination of features of the biological sample represented by digital images and grading such features. The method 300 may be implemented in digital pathology systems to use consistent acquisition parameters to capture digital images of clinical samples. High throughput systems are presently capable of handling hospitals entire workflows. Single user devices have been described by these inventors as a means to bring the technology to a pathologist's desk. The method 300 may supplement the estimation and qualitative reasoning performed by the pathologist with quantitative analysis. Thus, to calibrate the algorithms of the method described below, pathologists have been observed, tested and interviewed and have provided feedback on the performance, function, utility and design of the tool.

At 302, a primary diagnosis may be performed. A pathologist may identify the primary diagnosis using ancillary and addendum notes from the patient's medical record. The patient information may be ascertained by reading, e.g., a barcode associate with a physical patient file. The patient information may indicate that the primary site is a breast. This may initiate a specific breast cancer algorithm from among the cancer grade library stored in, e.g., the one or more databases 112.

At 304, a tissue of interest may be identified to perform the initial region classification. For example, the pathologist may visually determine the tissue of interest to locate tumor cells, nodules, calcifications, necrosis, inflammation, and a number of identifiable characteristics specific to that disease site. The algorithm has been trained by pathologists to locate the same regions of interest. In particular, the present disclosure leverages pattern recognition capabilities to precisely identify tumor cells. This provides investigators an opportunity to know the precise number of tumor cells in a given sample, the area in 2D, the percentage versus other tissues. This has proven to be an extremely valuable and reliable tool for clinicians and researchers who routinely use this information to make the best possible decisions.

Figure 3B:
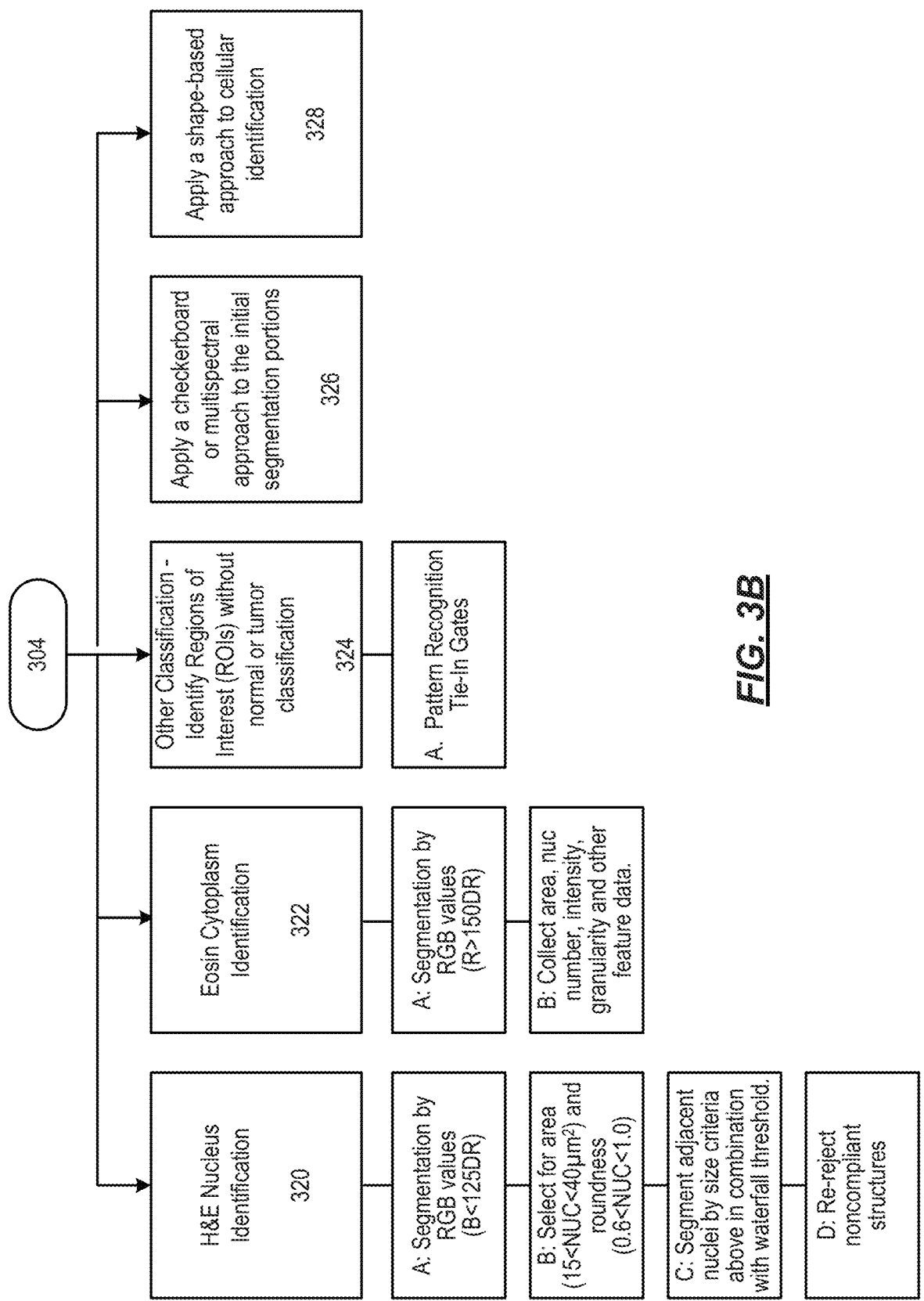
FIG. 3B illustrates an operational flow diagram of example processes that are performed at 304 in FIG. 3A.

The initial region classification at 304 may include one or more of the following sub-processes, as illustrated in the operational flow of FIG. 3B. It is noted that the present disclosure is not limited to any ranges provided, rather they are merely provided as examples:

I. Hematoxylin and Eosin (H&E) Nucleus Identification (320):
  A: Segmentation by RGB values (B<125 DR)
  B: Select for area (15<NUC<40 μm$^2$) and roundness (0.6<NUC<1.0)
  C: Segment adjacent nuclei by size criteria above in combination with waterfall threshold.
  D: Re-reject noncompliant structures
    1. Density Dependence
      a: Calculate nuc centroid to centroid shortest distance
      b: Identify regional density>tissue of interest hyperplasia
      c: Threshold density for tumor of interest
        i. Tumor Region Classification
          aa: Compare tissue of interest normal library of nuc features and density with features and density of the AOIs identified and reclassify accordingly.
          ab: Optional QC checkpoint II. Eosin Cytoplasm Identification (322):
  A: Segmentation by RGB values (R>150 DR)
  B: Collect area, nuc number, intensity, granularity and other feature data.
    1. Nuclear:Cytoplasmic ratio (N:C) Ratio
      a: Grow nuclei into cytoplasm to create super level cell with constraints
      b: Cleanup non-nucleated ROIs
      c: Quantify N:C area measure
        i. Non-Tumor Abnormal Classification—Reclassify any features not identified as normal or tumor via tissue specific library features (inflammation, reactive stroma, fibroblasts et cetera)

III. Other Classification—Identify Regions of Interest (ROIs) without normal or tumor classification (324):
  A. Pattern Recognition Tie-In Gates
    1: Clean up non-interest ROIs
    2: Reconfirm classified ROIs
    3: Second cleanup and segmentation review
    4: Optional QC checkpoint
      a. Other Classification—Classify outliers IV. Checkerboard or multispectral approach (326).

V. Shape-based approach to cellular identification to discern the nuclei in order to count the nuclei (328). This may be performed in addition to, or optionally instead of, an intensity/color approach to identify the cells at 322.

In accordance with the initial region classification process(es), breast epithelial cells can be identified as normal, hyperplasia, atypical hyperplasia, ductal carcinoma in situ, lobular carcinoma in situ, invasive ductal carcinoma, tubular carcinoma, medullary carcinoma, mucinous carcinoma, metaplastic carcinoma, invasive criboform carcinoma, invasive papillary carcinoma, invasive micropapillary carcinoma, inflammatory breast cancer, Paget's disease of the nipple, or phyllodes tumor. These are the sixteen diagnostic presentations which may be identified. Any tissue regions which are not identified by one of these subtypes are classified as unidentifiable and are specifically highlighted for pathologist review. For simplicity of description, invasive ductal carcinoma (IDC) will be assumed as the diagnosis (80% of all invasive breast cancers). The step for grading cancer is not which subtype is present, but what the grade of that subtype is presenting.

At 306, the tumor region is surveyed to assess nuclear pleomorphism. This is cancer cell classification within the method 300. The tumor cells are segmented within the (IDC) region of interest by first identifying the nuclei using additionally trained nuclear parameters including but not limited to: size ($25\ \mu m2 < IDC < 60\ \mu m2$); hematoxylin counterstain ($160\ DR < layer3 < 210\ DR$); shape ($0.65 < R < 1.0$; $0.45 > L > 1.0$); texture ($0.7 < Haralick < 0.9$); nucleus to cytoplasmic ratio ($0.8 < N:C < 4$). Each nucleus generates as few as four statistics (area, intensity, roundness, texture), but as many as 210. These features are used to create a nucleus feature list, and the mean, median, mode, standard deviation and significant outlier statistics area generated. These values are compared to the same features in the IDC of the breast library for normal nuclei. The abnormal values are compared to the normal range, and to itself to determine the variability in nuclear features present. A nuclear pleomorphism score is generated to range between 1 and 100 in one-tenth increments. Samples with more pleomorphic cells have a higher score. The companion diagnostic pleomorphic score is reduced back to the current gold standard in tertiles.

Cancer cell classification may be performed as follows:
1: Create new level for cancer cell analysis
2: Pull nuclear and cyto features into cell level
   A. Determine Nuclear Waterfall
      1: Load nuclear identification and feature data
      2: Create distribution plot data for 16 identified nuclear features
         a. Score Pleomorphism—Score distribution plot against tissue of interest library
            i. Score I: Nuc Pleo—Rate nuc pleo into tertiles for tissue of interest
   B. Mitotic Density
      1: Identify mitotic figures (length, density, L:W ratio et cetera)
      2: Chessboard WSI into 400× HP fields
         a. Counts per Field—Count identified mitosis per HP field
            i. Score II: Mitotic Rate—Compare number identified in 10 highest density HP fields and rank into known tertiles
   C. Regions Fractals
      1: Identify library of fractal analysis of structure for tissue of interest
      2: Run fractal dependent analysis over WSI
         a. Score and Bin Acinar Structure—Bin tertiles of fractal results
            i. Score III: Tubule Formation—Score results in tertiles against library of tissue of interest At 308, the cancer cell classification test and validation steps are used to correctly segment and identify tumor cells, and compare the physical traits of those cells with the normal standard. For example, the most complex scoring algorithm is the Nottingham Breast Cancer Score. This score incorporates three criteria: nuclear pleomorphic, tubule formation, and mitotic count, as opposed to the Gleason score which measures patterns of anaplasia (similar to tubule formation mentioned above) or simple grades which quantify how different cancer cells look compared to normal cells of the same type.

Each of the Nottingham criteria is given a score between one and three (higher scores are more perturbed). The sum of these scores (3-9) is then re-segmented into low grade (I=3-5), moderate grade (II=6-7) and high grade (III=8-9) Nottingham Grades.

Thus, by using an extensive database of well over 15,000 tissue samples and complex histology, pattern recognition software and algorithms have been designed and optimized to recognize tumor regions within histology samples, segment the individual nuclei, and report the tumor burden as the number of tumor cells, the area of tumor versus other cell types, and the percentage of tumor cells. To achieve accuracy and reliability of each algorithm, exhaustive tests and validation steps are used to correctly identify and segment tumor cells, and compare the physical traits of those cells with the normal standard. Each value is reported with a specificity and sensitivity metric to be used to ensure the highest quality analysis for heterogeneous sample qualities.

Figure 4A:
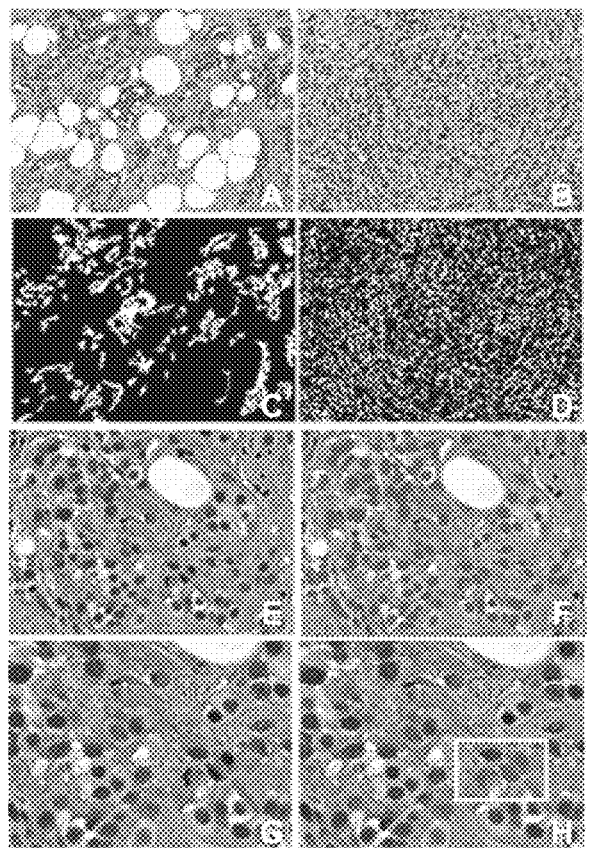
FIGS. 4A and 4B illustrate several representative graded digital images of biological samples.
Figure 4B:
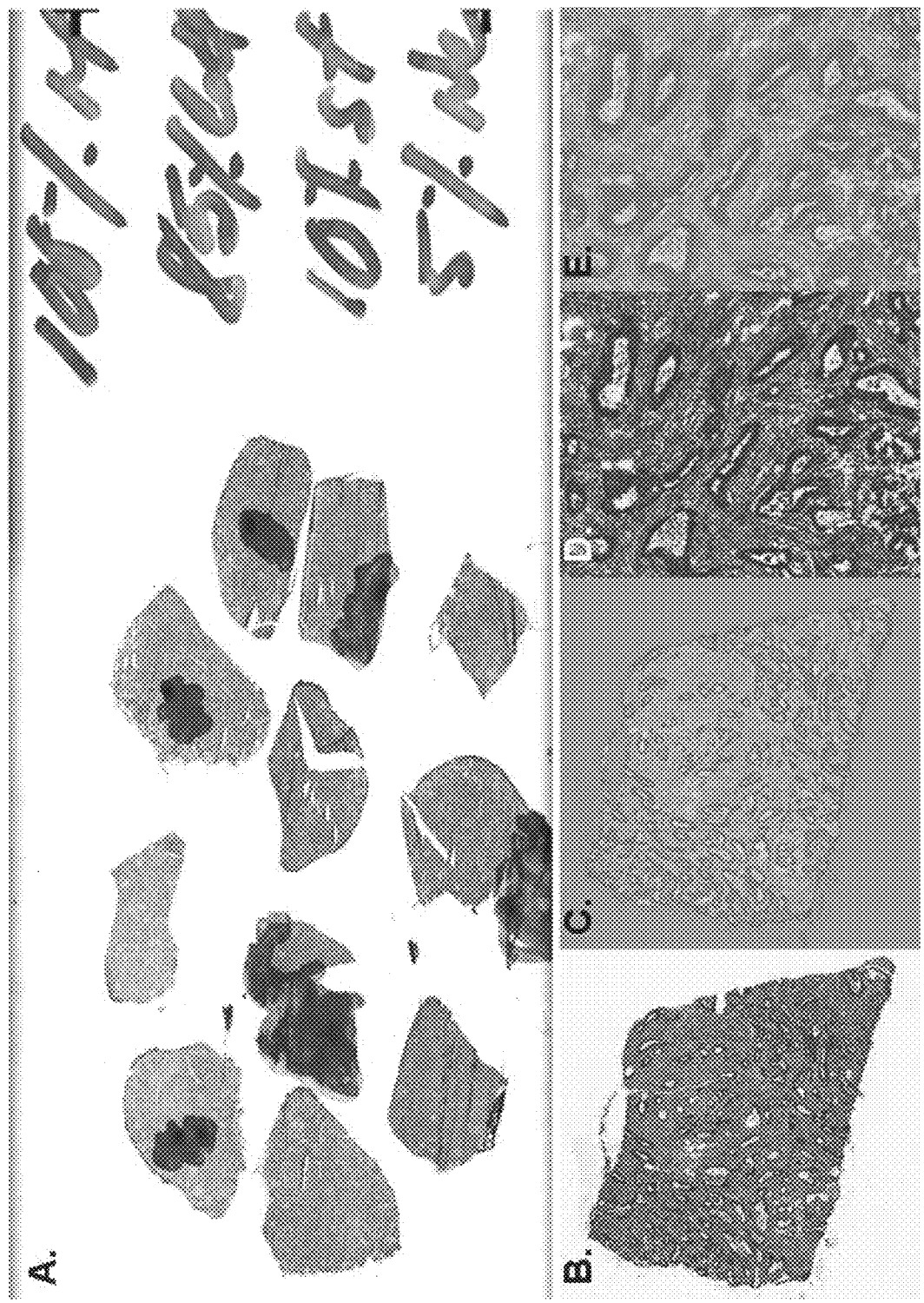

FIGS. 4A and 4B illustrate several representative graded digital images of biological samples. In FIG. 4A, image A is a grade I invasive breast cancer; image B is a grade III invasive breast cancer; image C is a binary masked evaluation of acinar formation grade I; image D is a binary masked evaluation of acinar formation grade I; image E is a grade II nuclear pleomorphism; image F is a nuclear identification for evaluation of nuclear size, roundness and nucleus: cytoplasm ratio; image G is a grade III mitotic count; and image H is a mitotic figure identification and evaluation of grade. The method 300 mimics the above by first identifying the tumor region, segmenting the cells and addressing the properties of nuclear features, tubule formation and the exact number of mitotic counts per 10 (40×) high powered fields (as described by the AJCC guideline).

In FIG. 4B, image A illustrates how pathologists select the regions of interest with a histology pen by drawing directly on the glass slide. However, even tumor regions of tissues are made up of a complex network of heterogeneous cell types including, but not limited to, stroma, fibrosis, inflammation, vasculature, blood cells, bone and cartilage, adipocytes or fat cells, muscle et cetera. When a tissue is selected for downstream analysis, each of these cell types plays its own important role in the outcome and subsequent data. With the advent of histological pattern recognition, a quantitative tool has been developed to identify individual cancer cells from the rest of the tissue cell populations with precision. Image B depicts an H&E whole slide image of colon cancer with millimeter resolution. Image C is a green mask of epithelial tumor and yellow mask identifying other tissues. Images D and E depict the same sample at micron levels of resolution. Each cell may be counted individually to establish a precise tumor burden.

The tumor region is surveyed by the pathologist and 10 high power fields (40×) are reviewed in regions estimated to include the highest rate of mitosis, and the number of mitotic events is counted. 0-9 mitoses score 1; 10-19 mitoses score 2; 110 or more score 3.

In accordance with some implementations, the system 100 has the entire IDC tumor available to survey, and the area of one high power field (hpf) is known. The area of the hfp depends on the scanning instrument used. In this example the Aperio ScanScope XT will be assumed (0.37 μm2/pixel) and the field is tiled into hpf. Each field is surveyed for mitotic figures with the features including but not limited to: size (10 μm2<IDC<20 μm2); hematoxylin counterstain (220 DR<layer3<255 DR); shape (0.00<R<0.45) (0.85>L>1.0); with a defined mitotic figure within 4 μm. The count is calculated for each pair in each hfp and the fields with the largest mitotic counts are identified and the figures are summed. The results are compared with the grade system standard as described for scores 1-3 above.

The tubule formation is estimated by the pathologist as either the majority of the tumor (>75%), a moderate degree (10-75%) or little to none remaining (<10%). The companion diagnostic method 300 determines tubule formation by calculating the larger structure of the tumor in surface area box counting fractal dimensions to calculate and record the complexity of the objects. The system 100 may also determine the neighboring objects for each cell, which can be described as near (μ2 μm2) or distant >2 μm2) and the direction of distance. This is used to create the gland formulation score which is based on the premise that cells with two neighbors on opposite sides, but not on the other sides, are likely cells within glands, whereas cells with more than two near cells, or no near cells, are likely part of a less organized structure. The fractal dimension and gland formulation score are combined to determine the tubule formation. IDC cells are then calculated as a whole to fit back into the grading criteria described for the pathologist above.

The pathologist tallies each of the criteria above to calculate a sum Nottingham score. The system 100 may do the same, and draft a simple report (at 310) for each of the three sub-scores and the ultimate Nottingham Grade of I, II or III. The raw data are retained as ancillary data to be reviewed at a later date as needed. The electronic record is imprinted as a layer with the digital slide, and can be linked to the Laboratory Information Management System and populated with the patient history, images, and other ancillary data.

In some implementations, the system 100 may apply the primary tumor site's accepted grade(s) to each slide in patient case, and compares the results to the library of known normal descriptions for that tumor morphology. The comparison score is then binned, e.g., into the same scoring mechanism accepted for use by the AJCC and CAP guidelines and the quantitative score is recorded in a simple digital record sheet. In this case the algorithms run sequentially until all libraries for the primary site are exhausted and recorded.

Thus, as described above, the method 300 works seamlessly with digital whole slide scans from either instrument throughput type to create a simple, easy to use score which pathologists may then use as a companion diagnostic tool. As such, pathologists will have a simple, easy to use, companion diagnostic to enhance reliability, repeatability, accuracy and quantification is paramount. Similarly, pathologists will be provided with a tool which can insure a more accurate diagnosis. Furthermore, the present disclosure lays the groundwork for grading criteria, feature analysis and biological progression of disease indicators which will ultimately increase the precision of pathologist's evaluations and will more carefully examine the needs of individual patients.

Figure 5A:
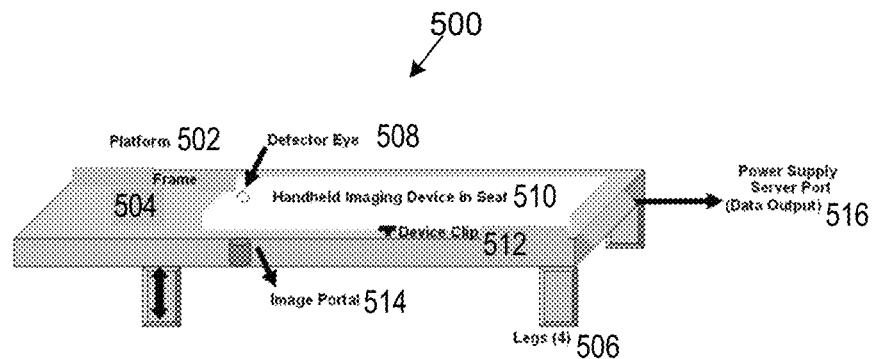
FIGS. 5A-5C illustrate an desktop slide scanning device.
Figure 5B:
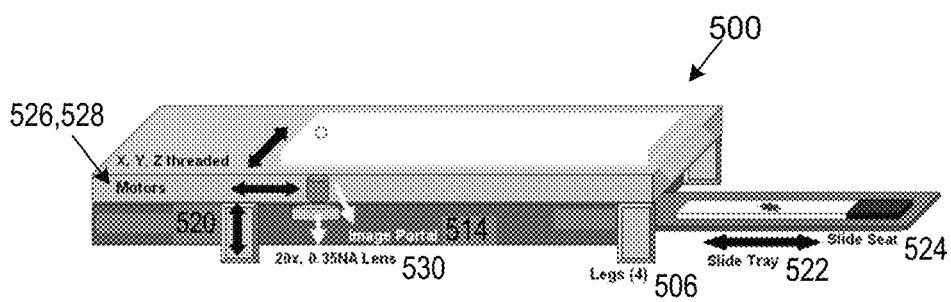
Figure 5C:
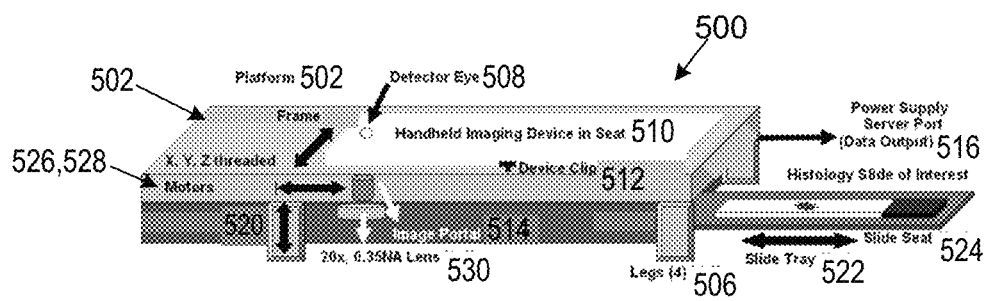

Now with reference to FIGS. 5A-5C, there is illustrated several views of the desktop slide scanner 500 of the present disclosure. As shown in FIGS. 5A-5B, the desktop slide scanner 500 (platform 502) includes a frame 504, which is the structure of the desktop slide scanner 500, and an imaging housing 520, which enables detection of the sample at sufficient magnification and resolution and enables functionality of the specimen location motors, and the handheld device itself.

The frame 504 is a desktop base device having dimensions of approximately 6" W×11" L×3" H, or other dimensions such that it suitably operates within a desktop environment. The frame 504 may be made from a suitably lightweight rigid material, such as aluminum, plastic, etc., and supported by four legs 506 at each corner of similar materials. The legs 506 may be, e.g., 2" in height. On the top of the frame 504 is a personal communication device seat 510, having dimensions suitable to receive a handheld or portable device, such as a smart phone, tablet device, etc. The seat 510 receives the portable device to a light a detector (e.g., a camera) embedded within the particular portable device with a detector eye 508. Integration may be achieved with handheld/portable devices, such as iPhones, iPads, Android devices, BlackBerrys, etc. or any tablet-style computer. As will be described below, using the built-in detector (e.g., camera 108) of handheld/portable devices, digital images may be taken of slides loaded into the desktop slide scanner 500. The camera 108 may be a CCD (Charge Coupled Device) or a CMOS (Complementary Metal Oxide Semiconductor). The aforementioned may be achieved through a combination of hardware and software, as described below. Optional device clips 512 may be provided on each side of the seat 510 to secure a handheld/portable device to the frame 504.

Within the device seat 510 there is provided three openings. A first opening is located at the camera detector eye 508. A hole may be fitted with a rubber seal formed specific to the dimensions of the CCD/CMOS detector of the handheld device received by the seat 510. The seal excludes light from entering the imaging field during use. Second and third openings are designed to allow pass-through of two cords, one for a network connection (see, FIG. 6) and the second for a power connection 516. Where the connection cords are considered semi-permanent (i.e., are not removed after each use), these can be outfitted with spring loaded cord seats in order to make connecting the device to the cords an effortless operation. In some implementations, power cords may not be necessary if, e.g., powerpad technology is available to fit in seamlessly within the seat 510. Still further, the wired network connection may be alternatively replaced by a wireless connection, such as, Wi-Fi, 3G, 4G, etc.

With reference to FIGS. 5B-5C, the imaging housing 520 may be formed as a light-tight enclosure with approximately the same lateral dimensions of the frame 504. The imaging housing 520 serves to move a biological sample disposed on a slide into the imaging field, where the sample may be magnified to be detected. For example the slide may be a standard glass microscopy slide sample (20 mm×50 mm×2 mm). In order to move the slide, the imaging housing 520 is outfitted with a laterally sliding tray shown as a slide holder 522. The slide is placed into, e.g., a 1 mm recessed 20 mm×50 mm tray 524 to hold the sample in a known, stationary position. The slide tray 524 may be made from aluminum or other lightweight material, and is mounted under the frame 504, and within the imaging housing 520. The slide tray 524 may be mounted on track threaded spiral guides 526 moving the length of the x-direction (e.g., 11") and mounted in the y-direction (6") axis by two mounting clips on each axis. The mounting clips may be made from aluminum or other lightweight material. The tray 524 may be outfitted with a third, z-axis step motor 528 which moves in, e.g., 0.2±0.01 µm increments. It is noted that any drive mechanism may be used to move the tray 524, such as rack-and-pinions, belts, chains, linear motors, ball screws, and fluid pressure cylinders.

Magnification may be achieved through an imaging portal 514. The imaging portal 514 may include a low-profile super optical telecentric lens with 20× magnification, 0.35 numerical aperture, and a 36.5 mm working distance. The lens may be mounted on the underside of the imaging portal 514. In some implementations, the lens may hinge on its own motor, which may be instructed by software to move the lens in and out of place as image acquisition is initiated. A light source may be provided within the imaging housing 520, for example, a light-emitting diode or a xenon lamp. Light from the light source may be reflected on a mirror, or directly illuminated, on the sample disposed on the slide of interest.

Figure 6:
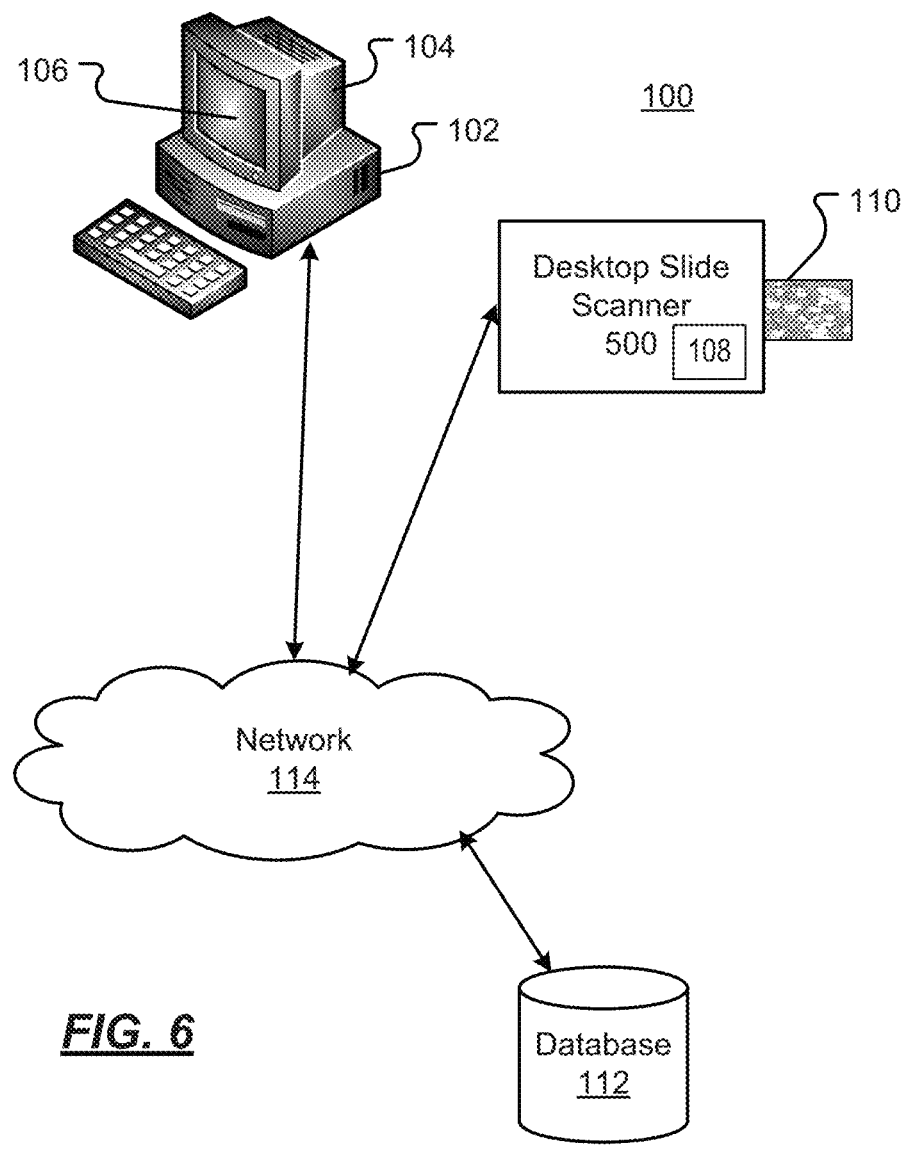
FIG. 6 illustrates an exemplary environment in which the desktop slide scanning device may operate.

FIG. 6 is a block diagram illustrating another exemplary digital image acquisition system 600. Moreover, like reference numerals designate corresponding components, as described above and will not be described again. The system 600 may include a desktop slide scanner 500 that incorporates the camera 108. As will be appreciated, the camera 108 may be stand-alone camera or part of handheld/portable device as described above in FIGS. 5A-5C. The desktop slide scanner 500 is adapted to capture digital images of slides 110 in cooperation with the camera 108 of, e.g., a handheld/portable device. Alternatively or additionally, the desktop slide scanner 500 may be adapted to capture digital images under the command and control of the one or more computers 102 connected over the one or more communications networks 114.

Operation of the Desktop Slide Scanner 500

Figure 7:
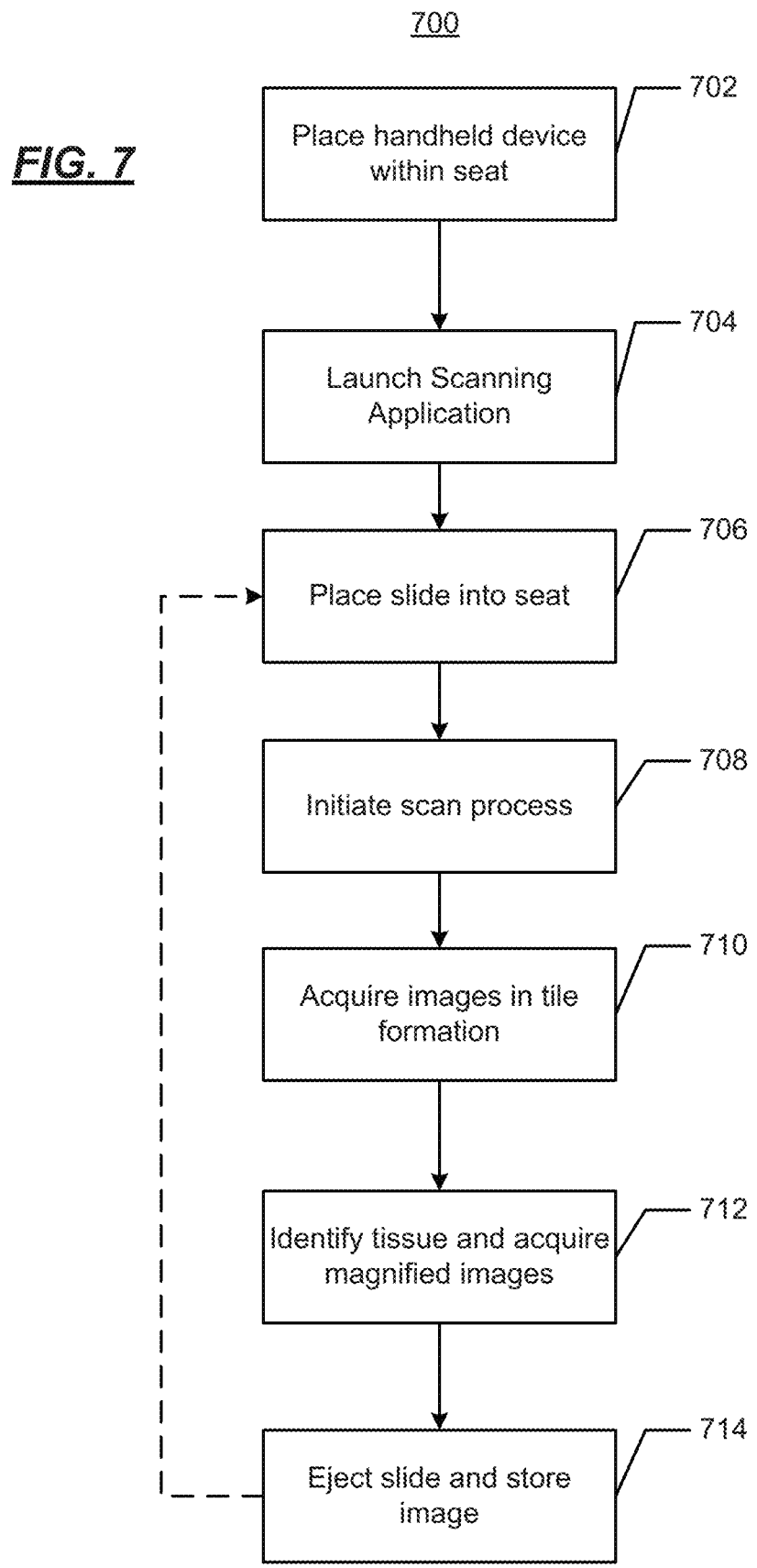
FIG. 7 illustrates an operational flow diagram that illustrates a method for scanning slides using the desktop slide scanning device of FIGS. 5A-5C.

FIG. 7 is a flow diagram illustrating a process for obtaining a digital image from a slide having a biological sample disposed thereon. Generally, the operation includes one or more of the operations of slide loading, tissue identification, sample focusing, digital imaging, data transfer for the purposes of data management, and analysis. In some implementations, the function may be driven by the handheld/portable device 108 itself. For example, drivers scripted for the iOS (Apple) operating system and Android applications may communicate with a scan button provide on the desktop slide scanner 500 and the drive motors thereof. Alternatively or additionally, the one or more computers 102 may operate the desktop slide scanner 500 by communication with the handheld/portable device or the desktop slide scanner 500 itself. Alternatively or additionally, operation of the desktop slide scanner 500 may be initiated by a touch of a display or button of the handheld/portable device or actuation of a graphical element on the display 104.

At 702, a user places a handheld/portable device on the seat. The user may place the device 108 on the seat 510 and allow spring loaded cord injectors to plug-in to the device. This action may which turn the device 108 on. At 704, the scanning application is launched. This may occur automatically upon seating the device 108 or manually by user action. At 706, the user loads a slide into the tray seat and actuates a scan button. This initiates the scan process at 708. During the scan process, the tray 522 is moved to position the slide such that a center of the image portal 514 is over a calibration area and a background image may then be captured. The lens position is checked and moved into position distant from the image portal.

At 710, images of the slide are acquired. Here, the slide 110 is then moved such that the top left of the slide 110 is placed under the image portal 514. Images are taken in tile formation from left to right and top to bottom to cover the entire slide 110. Alternatively, an array of detector chips may be provided, or line scanning detection performed to acquire the images. At 712, the resulting stitched image is then processed through a 'find tissue' algorithm within the device application. The find tissue algorithm highlights objects with more contrast than the calibration image in addition to an area larger than an area determined by the user or default setting. Coordinates of these regions are auto-targeted for scanning. A checkerboard coordinate map is established in the software with the known pixel size dimensions for the device used. Where tissue is not found, the user may optionally manually select scan regions. Next, the lens position is moved into the image portal window. From left to right and top to bottom each coordinate on the map is imaged at, e.g., 20× magnification or other suitable magnification to create magnified images of the detected tissue regions of the slide 110.

At 714, the slide is ejected. A new slide may be inserted where the process returns to 706 or the process may end. Each image may be cached to the database 112 over the network 114. In some implementations, the image may be cached to the device 108 or computer 102. The device 108 or computer 102 may display the information on the screen or display 104, and the low magnification pictures may be saved for non-network database review and algorithm queuing.

Thus, as described above, there is a simple, easy to use, high resolution whole slide imaging device for individual use. The small footprint is ideal for single use. The device integration is efficient, and takes advantage of the optimized imaging, computing and software scripting efforts provided by Apple and Android. The one touch ease of use is ideal to meet the needs of pathologists without the desire to use complex instrumentation. The optical lens is capable of matching magnification, NA and WD in a confined space. Furthermore, this lens is capable of utilizing a myriad of detectors for numerous devices.

Further, the present disclosure describes a system and methods that address a number of current challenges including, but not limited to: 1) losing or damaging glass slides; 2) subjective or inadequate documentation of specific regions with spatially limited still frame digital imaging; 3) inability to document and manage one's own cases; 4) inefficient sharing between colleagues; 5) reliance on technicians unfamiliar with your personal workflow. In addition it makes several new opportunities available including 1) quantifiable analysis by FDA approved algorithms; 2) documentation for tumor board, departmental meetings or other sharing opportunities; 3) single button ease of use and others.

FIG. 8 shows an exemplary computing environment in which example implementations and aspects may be implemented. The computing system environment is only one example of a suitable computing environment and is not intended to suggest any limitation as to the scope of use or functionality.

Numerous other general purpose or special purpose computing system environments or configurations may be used. Examples of well known computing systems, environments, and/or configurations that may be suitable for use include, but are not limited to, personal computers (PCs), server computers, handheld or laptop devices, multiprocessor systems, microprocessor-based systems, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 8, an exemplary system for implementing aspects described herein includes a computing device, such as computing device 800. In its most basic configuration, computing device 800 typically includes at least one processing unit 802 and memory 804. Depending on the exact configuration and type of computing device, memory 804 may be volatile (such as random access memory (RAM)), non-volatile (such as read-only memory (ROM), flash memory, etc.), or some combination of the two. This most basic configuration is illustrated in FIG. 8 by dashed line 806.

Computing device 800 may have additional features/functionality. For example, computing device 800 may include additional storage (removable and/or non-removable) including, but not limited to, magnetic or optical disks or tape. Such additional storage is illustrated in FIG. 8 by removable storage 808 and non-removable storage 810.

Computing device 800 typically includes a variety of computer readable media. Computer readable media can be any available media that can be accessed by device 800 and include both volatile and non-volatile media, and removable and non-removable media.

Computer storage media include volatile and non-volatile, and removable and non-removable media implemented in any method or technology for storage of information such as computer readable instructions, data structures, program modules or other data. Memory 804, removable storage 808, and non-removable storage 810 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media may be part of computing device 800.

Computing device 800 may contain communications connection(s) 812 that allow the device to communicate with other devices. Computing device 800 may also have input device(s) 814 such as a keyboard, mouse, pen, voice input device, touch input device, etc. Output device(s) 816 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the processes and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be affected across a plurality of devices. Such devices might include PCs, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A desktop slide scanner, comprising:
    a portable device comprising an embedded imaging device and a detector eye;
    a frame that defines a seat into which the portable device is disposed, wherein the detector eye of the portable device is configured to align the portable device with the frame;
    an imaging portal mounted to the frame that includes a lens having a predetermined magnification, wherein, when the portable device is aligned with the frame, the imaging portal is aligned with the embedded imaging device; and
    a light-tight enclosure that is received within the frame, the light-tight enclosure further including a moveable slide tray having a slide seat adapted to receive a slide, wherein the slide tray is moved within the light-tight enclosure and imaged by the embedded imaging device, and wherein the images are magnified at the predetermined magnification by the lens within the imaging portal.

2. The desktop slide scanner of claim 1, further comprising a seal that forms around the embedded imaging device of the portable device to exclude light from entering an imaging field during use.

3. The desktop slide scanner of claim 1, further comprising a network connection provided to the portable device to transfer images to a remote repository.

4. The desktop slide scanner of claim 1, wherein the slide tray is moveably mounted on a track.

5. The desktop slide scanner of claim 1, further comprising a step motor to move along an axis of the desktop slide scanner in predetermined increments.

6. The desktop slide scanner of claim 1, wherein the imaging portal provides a predetermined level of magnification.

\* \* \* \* \*